United States Patent [19]

Bicher

[11] 3,999,284
[45] Dec. 28, 1976

[54] METHOD FOR MAKING A POLAROGRAPHIC SENSING MEANS

[75] Inventor: Haim I. Bicher, Charleston, S.C.

[73] Assignee: Mediscience Technology Corporation, Cherry Hill, N.J.

[22] Filed: Apr. 10, 1975

[21] Appl. No.: 566,733

Related U.S. Application Data

[62] Division of Ser. No. 365,431, May 31, 1973, Pat. No. 3,878,830.

[52] U.S. Cl. .................................. 29/570; 29/588; 204/195 P; 204/195 B
[51] Int. Cl.² .......................................... B01J 17/00
[58] Field of Search .......... 29/570, 588; 204/195 P, 204/195 B

[56] References Cited
UNITED STATES PATENTS

| | | | |
|---|---|---|---|
| 3,259,124 | 7/1966 | Hillier | 204/195 B |
| 3,380,905 | 4/1968 | Clark | 204/195 P |
| 3,800,410 | 4/1974 | Niedrach | 29/570 |

*Primary Examiner*—W. Tupman
*Attorney, Agent, or Firm*—Jacob Trachtman

[57] ABSTRACT

A catheter system for blood gas monitoring and the method of making same comprising a polarographic sensing means having a body, first and second conductors supported by the body and each respectively having an exposed conducting surface at a region of the body, electrolytic material supported by the body at said region in contact with the exposed surfaces at the first and second conductors, and a membrane supported by the body extending over the region of said body covering the electrolytic material. The membrane is pervious to oxygen in the fluid system and semi-pervious to water. The electrolytic material is anhydrous prior to use of the device and is activated by immersing in a aqueous solution just before use. The sensing means is at the end of a cable carrying the conductors which cable has its other end joined to the connector end of a terminal or transport unit. The end opposite the connector end of the unit has a securing means for attaching the unit to the hub end of a catheter through which the sensing means and cable are receivable.

9 Claims, 10 Drawing Figures

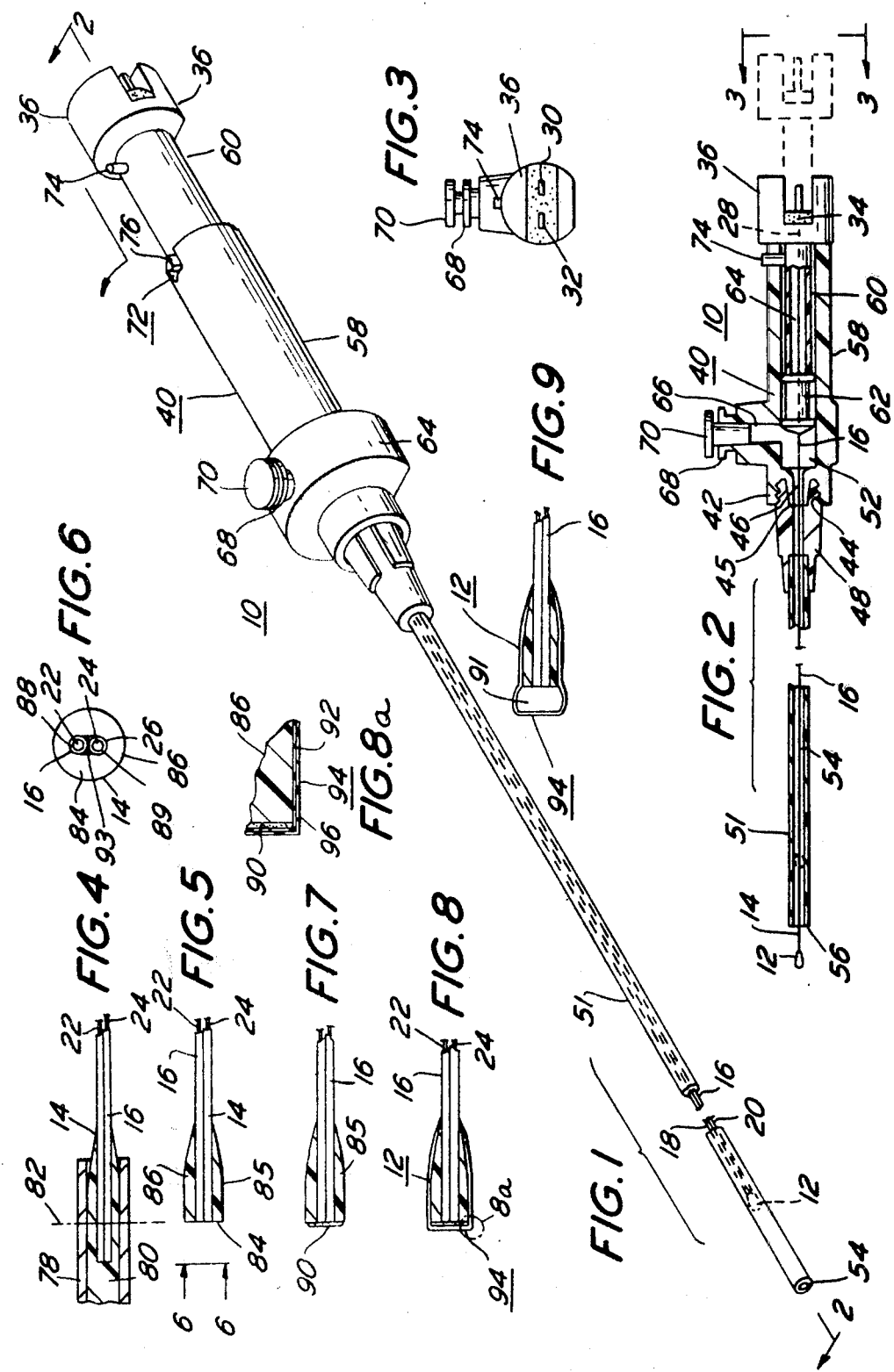

METHOD FOR MAKING A POLAROGRAPHIC SENSING MEANS

This is a division, of application Ser. No. 365.431 filed May 31, 1973, now U.S. Pat. No. 3,878,830.

The invention relates to a catheter system for blood gas monitoring and method of making same and particularly a system for monitoring and measuring the partial pressure of oxygen in the blood system which provides a sensing head with a dry electrolyte for long shelf life which can be activated prior to use by emersion in a aqueous solution and method of making and activating the sensing head.

The constant monitoring of respiratory gas tensions in the circulating blood is vital for determining patient responses during anesthesia, certain surgical procedures and the treatment of heart, pulmonary and metabolic diseases, as well as for assisting positive pressure breathing and during many medical emergencies including shock or trauma. Heretofore, no device has been available for fulfilling such needs in a practical, reproducable, and economical manner. The present invention provides such a catheter system which is readily implantable and has a disposable catheter and sensing means for determining gas tension in the blood, particularly the partial pressure of oxygen and can be implanted in the vein or artery, or in the tubing attached to a heart-lung machine or to any similar profusion apparatus.

It is therefore a principal object of the invention to provide a new and improved catheter system and method of making same for blood gas monitoring which is highly reliable and may easily be implanted in the region where the blood system is to be monitored.

Another object of the invention is to provide a new and improved catheter and method of making same which may be inexpensively produced and has a disposable catheter and sensing unit.

Another object of the invention is to provide a new and improved catheter system and method of making same for monitoring the partial pressure of oxygen in the blood system in-situ or at a selected point or location in the circulatory system with desirable accuracy over an extended period of time.

Another object of the invention is to provide a new and improved catheter system and method of making same for blood gas monitoring which provides a relatively long shelf life and may be readily activated just before use by immersion in an aqueous solution.

Another object of the invention is to provide a new and improved catheter system for blood gas monitoring which allows a sensing head to be threaded through a catheter or cannula already in place in the patient without disturbing other catheter functions.

Another object of the invention is to provide a new and improved catheter system for blood gas monitoring which may readily be calibrated in-situ, provides for obtaining blood samples and for infusing fluids therethrough without interfering with the monitoring and measuring functions.

Another object of the invention is to provide a new and improved catheter system for blood gas monitoring which includes a delivery or transport unit for being secured with a catheter and controlling the placement of the sensing head selectively within the catheter or extending beyond the catheter into the circulatory system.

Another object of the invention is to provide a new and improved catheter system for blood gas monitoring which permits the sensing head to be implanted with the insertion of a catheter or after a catheter has been implanted, and also allows the removal of the sensing means without requiring the removal or disturbing of the implanted catheter.

Another object of the invention is to provide a new and improved catheter system and method of making same for blood gas monitoring which is highly reliable in operation, provides good stability over an extended period of time, and may readily be calibrated to provide accurate read-out information.

The above and other objects of the invention are achieved by providing a catheter system and method of making same for blood gas monitoring which has a polarographic sensing means or head comprising a body, first and second conductors supported by the body and each respectively having an exposed conducting surface at a region of the body, electrolytic material supported by the body at said region in contact with the exposed surfaces of the first and second conductors, and a membrane supported by the body extending over the region of said body and covering the electrolytic material. The membrane is provided with an inner layer which is pervious to oxygen in the fluid system and semi-pervious to water, and a gas pervious outer layer which is compatible with the blood system into which it is placed.

Prior to use of the sensing head, the electrolytic material is anhydrous or of crystalline form for providing long shelf life with minimized deterioration. The electrolytic material is activated by immersing the sensing head in an aqueous solution, which may be a saline solution, prior, to use. In the particular form illustrated, the electrolytic material is potassium chloride, and the inner layer of the membrane is made of polyvinyl formal with an outer layer of silicone elastomer.

The pair of conductors of the head each comprising a copper wire having a silver coating. One of the conductors is chlorinated to provide a silver chloride, copper chloride surface in contact with the potassium chloride electrolyte as one electrode, while the other electrode is formed by the silver clad copper wire, also in contact with the electrolyte. The pair of conductors of the sensing head are provided by one end of a cable which has an insulating coating of a flexible material such as Teflon. The cable is connected at its other end to a terminal or transport unit which provides a connector for electrically detachably joining the wires of the cable to read-out equipment which may digitally indicate information derived from the sensing head, and also provide the bias potential utilized for operation of the sensing head.

The transport unit also has a first end providing a connector for threadedly engaging the hub of a cannula or catheter through which the cable and sensing head are threaded, and a cavity for communicating through the opening of the catheter to the circulatory system. The terminal unit is also provided with a plunger or piston which is received within the chamber and may be longitudinally moved for extending the sensing head from within the catheter to a position beyond the end of the catheter for making measurements in-situ. The piston when it is in its retracted position may be locked to avoid movement of the sensing head.

The terminal unit is also provided with a port communicating with its chamber which allows the drawing of blood samples through the catheter, and also for the infusion of fluids into the circulatory system as may be required.

The method of making the sensing means of the invention includes the steps of forming a body with first and second spaced electrodes providing exposed surfaces at a region of the body, affixing an anhydrous electrolytic material over the exposed surfaces of the electrodes on the body, securing with the body a membrane which is semi-pervious to water, enclosing the electrolytic material and the exposed surfaces of the electrodes. The anhydrous electrical material is affixed over the exposed surfaces of the electrodes by applying a wet elctrolytic material on the body over the electrodes and allowing it to dry prior to enclosing the electrolytic material by the membrane. The wet electrolytic material is comprised of potassium chloride gel which is dried to crystalline form. The membrane is formed by applying a solution of polyvinyl formal to the body over the anhydrous electrolytic material and drying same to form a coating which is semi-pervious to water and pervious to oxygen in an aqueous solution. An outer coating for the membrane is formed by the additional step of applying a silicone solution over the polyvinyl formal coating and allowing same to dry.

The method for forming the body of the sensing means with first and second spaced electrodes includes providing a cylindrical mold having an opening along its longitudinal axis and positioning in spaced axial extending relationship therein the first and second conductors, filling the opening of the mold about the conductors with a epoxy material in unset form and permitting the epoxy material to set and harden, severing the mold, the epoxy material and conductors extending therethrough, along a plane perpendicular to the longitudinal axis of the mold, providing the conductors with an exposed surface at a flat surface region of the body, and removing the remaining mold from about the body.

The method of the invention also includes the step of applying an aqueous solution to the outside of the membrane for activating the electrolytic material of the sensing means by passage of water through the membrane, prior to the utilization of the sensing means for blood gas monitoring.

The foregoing and other objects of the invention will become more apparent when the following detailed description of the invention is read in conjunction with the drawings, in which:

FIG. 1 is an enlarged perspective view of a catheter system for blood gas monitoring embodying the invention, FIG. 2 is a sectional view of reduced size taken on the line 2—2 of FIG. 1, FIG. 3 is an end elevational view taken on the line 3—3 of FIG. 2, FIGS. 4, 5, 6, 7 and 8 are enlarged sectional views illustrating the method of making the sensing head of the inventon, FIG. 8a is an enlarged portion of FIG. 8, and FIG. 9 is an enlarged sectional view of the sensing head similar to that shown in FIG. 8 after the electrolytic material has been activated by immersing the head in an aqueous solution.

Like numerals designate like parts throughout the several views.

Referring to the figures, the catheter system of the invention comprises a sensing means 10 having a sensing head 12 at the end 14 of a flexible cable 16 including double parallel insulated lines 18 and 20 with wire conductors 22 and 24. The cable 16 may have an outer insulating wall 26 of a plastic material which is compatible with the blood system, such as that commercially known as Teflon. The conductors 22 and 24, may be made of any suitable conducting material, and in the specific embodiment disclosed comprises copper wire which is silver plated. Such a cable having AWG size 36 wires is commercially available from Phoenix Wire, Inc. as catalog number 36TDQ.

The conductors 22 and 24 at the other end 28 of the cable 16 are secured with and electrically connected to the posts 30, 32 of a male connector 34 which is located at the rear end 36 of a terminal or transport unit 40. The front end 42 of the transport unit 40 provides an opening 46 and internal threads 44 for engaging the connecting end or hub 48 of a catheter 51. The opening 46 of the transport unit 40 communicates with a chamber 52 therewithin. The chamber 52 communicates with the opening 54 of the catheter 51 which opening 54 extends from the connector end or hub 48 to the distal end 56 thereof. The chamber 52 of the transport unit 40 extends in the longitudinal direction within a cylindrical portion 58 of the transport unit 40.

The end 36 of the unit 40 is provided with a plunger or piston 60 which extends into the chamber 52 and is movable therein in the longitudinal direction. The end of the piston 60 is provided with a rubber seal 62 for preventing leakage of fluid from the chamber 52. The cable 16 passes axially and in the longitudinal direction through the center of the seal 62 and a central opening 64 in the piston 60 to the connector 34. The cable 16 extends in the opposite direction through the chamber 52 and out of the opening 46 of the unit to the sensing head 12 at its other end 14. The sensing head 12 may be threaded through the opening 54 of a catheter 51 after which the connector end 48 of the catheter is threadedly engaged with the end 42 of the unit 40 as illustrated in FIGS. 1 and 2.

As also illustrated in FIG. 1, when the unit 40 is in its extended position, the head 12 is moved toward the end 42 of the unit, while when the unit 40 is in its compressed condition with the piston 60 fully received into the chamber 52, the sensing head 12 is extended away from the end 42 of the unit 40. This relative movement of the head 12 may be seen from the illustrations of FIG. 1, which shows the sensing head 12 within the opening 54 of the catheter 51, and FIG. 2 which shows the sensing head 12 extending from the end 56 of the catheter 51 so that it is positioned external to the catheter 51.

The terminal or transport unit 40 is provided with a radially extending portion providing a port 68, proximate to its connector end 42 which has a radially extending opening 66 communicating with the chamber 52. The port 68 may be closed by a stop plug 70 when not in use, as illustrated, and may be used for delivering or removing fluid through the catheter 51 when such use is desired.

The rear end 36 may be enlarged over the piston 60 to provide ease of handling and a stop abutment when the piston 60 is fully received into the chamber 52 of the cylinder 58. The unit 40 is also provided with a locking means 72 in the form of a pin 74 extending radially from the piston 60 proximate to the rear end 36 and a J-shaped grooved 76 in the cylindrical portion 58 for receiving the pin in the axially direction and locking same by relative rotation of the piston 60 and cylinder 58. Such locking action is important for preventing the relative movement of the piston 60 with respect to the cylinder 58 and in turn preventing the movement of the sensing head 12, especially when the chamber 52 is subjected to high fluid pressure.

The head 12 at the end of the cable 16 provides a sensing means 12 of the polarographic type. The head 12 is produced at the end 14 of the cable 16 in a manner illustrated by FIGS. 4 to 8 inclusive. The end 14 of the cable 16 is placed into the end of a tube 78. The tube 78 may be made of plastic material, such as polyethylene, forming a casting mold as shown in FIG. 4. Epoxy material 80 in its plastic state is placed within the opening of the tube 78 about the end 14 of the cable 16. The positioning the epoxy 80 within the tube 78 may be assisted by using a hypodermic syringe needle at the rear of the tube to suck up the epoxy material. After the epoxy has set and hardened and has dried for at least 8 hours, the tube 78, epoxy material 80 and the cable 16 are severed along a plane indicated by the dashed line 82 of FIG. 4. The plane along which the cut is made provides a surface 84 which is perpendicular to the extending direction of the cable 16.

The tube 78 is now removed leaving an epoxy cast or plug 86 at the end 14 of the cable 16 with a flat end surface 84. The end surface 84, as seen in FIG. 6, provides exposed perpendicular cross sections of the conductors 22 and 24 of the cable 16 each of which is respectively surrounded by an insulation layer 88, 89 which may be of Teflon and bound to each other by the intermediate joining plastic material 93 which may also be Teflon. Surrounding the cable 16 is the epoxy cast or plug 86. The plastic covering 88 of the cable 16 may be provided with a red coloring to distinguish the conductor 22 from the conductor 24 which is covered by a plastic material 89 which is colored green or any other distinguishing color.

The end 14 of the cable 16 with its cast epoxy body 86 and exposed conductors 22, 24 is immersed in a 0.05 HCL aqueous solution for two minutes while an electrical potential of 1 volt is applied at the other end of the cable 16 between the conductors 22, 24. The positive potential is applied to the conductor 22, while the negative potential is supplied to the conductor 24. This results in providing a silver chloride coating at the silver plated surface of the conductor 22 and copper chloride coating at the exposed copper surface to form the reference electrode. The silver plated copper conductor 24 is not affected by the chlorination operation thus performed and provides the other electrode of the head 12. The flat end surface 84 of the plug 86 is positioned to face upwardly and a drop of wet electrolyte 90' is placed thereon making certain the electrolyte 90' is not received over the cylindrical side wall 85 of the plug 86. The electrolyte 90' is allowed to dry to form a dry electrolyte layer 90 for approximately 2 hours. The electrolyte 90' applied is potassium chloride gel such as that commercially available from Beckman Instruments, Inc. as $PO_2$ Electrolyte No. 326590.

Upon drying, the potassium chloride electrolyte crystallizes to provide a layer of electrolyte on the surface 84 extending over and between, and in contact with the exposed chlorinated end of the conductor 22 and the exposed metallic end of the conductor 24 (see FIG. 7).

The plug 86 is dipped into a solution of 0.25 % "Formvar" in ethylene dichloride. The Formvar utilized is Formvar 15/95E, a polyvinyl formal which has an average molecular weight of 24,000 to 40,000, a solution viscosity (15% by wt.) of 3,000 to 4,500 cp., a resin viscosity of 37 to 53 cp., a specific gravity (23°/23°) of 1.227, a hydroxyl content expressed as % polyvinyl alcohol of 5.0 to 6.0 (D1396-58), an acetate content expressed as % polyvinyl acetate of 9.5 to 13.0 (D1396-58). and a formal content expressed as % polyvinyl formal of about 82. This product is sold by Monsanto Chemical Co. and is described in detail in the Monsanto Technical Bulletin No. 6070A.

It has been found desirable to repeat the dipping process by double dipping the plug 86 in the solution, at one minute intervals between double dippings, and holding the plug 86 in the upward direction and alternately in a downward direction between dippings. The coated material is allowed to dry for from 5 to 10 minutes to provide the inner layer 92 of the membrane 94. The layer 92 extends over the entire outside surface 85 of the epoxy material 86 and where the end surface 84 is covered by the dried electrolyte layer 90, it extends over and encloses the electrolyte 90 as shown in FIGS. 8 and 8a.

After the inner layer 92 is dried, the plug 86 is double dipped in a solution of 0.2 gram of "Silastic" to each cc of xylene and allowed to air dry for 24 hours. The Silastic used is commercially available from Dow Corning Corp. as Silastic Medical Adhesive-Silicone, Type A, Stock No. 891. This forms a second or outer layer 96 of the membrane 94. The outer layer 96 extends completely over the inner layer 92 and provides a surface which is compatible with the blood system into which the sensor head 12 is to be received for making measurements.

In operation, the sensor head 12 is activated just prior to its use by immersing it in an aqueous solution, which may be a saline solution. With the passage through the membrane 94 of water, the crystallized potassium chloride electrolyte 90 is transformed into the electrolyte 91 in its active liquid state. This transformation causes the expansion of electrolyte 90 to provide the wet electrolyte 91 as shown in FIG. 9. In the expanded form, the membrane 94 is stretched to provide the configuration illustrated in FIG. 9, and the sensing head 12 is now in condition for measuring tension or partial pressure of oxygen in the fluid system under consideration.

In the form illustrated, the sensing means 10 provides a intra-arterial catheter with a polarographic head 12 for measuring in-vivo, the partial pressure of oxygen in the blood. The sensing head 12 is provided with an outside diameter of 0.5 mm so that it may easily fit through a 20 gauge Teflon arterial canulla. The sensing head 12 may be placed in an artery by utilizing a catheter which had previously been implanted in the subject, or by positioning an arterial canulla or catheter with its implanted end at the location at which in-vivo measurements are to be taken.

Thus, for example, with the catheter 51 positioned in the artery as required, the cable 16 with the head 12 at its leading end 14 is threaded through the opening 54 of the catheter 51 by entering its terminal end or hub 48. At this time, the transport means 40 is positioned with its plunger 60 in its withdrawn or extended condition as shown in FIG. 1. After the cable 16 has been fully threaded through the catheter 51, its sensing head 12 is positioned as indicated by the dashed lines in FIG. 1 and the end 42 of the transport unit 40 is proximate to the threaded end or hub 48 of the catheter 51. The end 48 of the catheter 51 and the end 42 of the transport unit are threadedly engaged so that the protruding male portion 45 of the transport unit 40 is received into and securely sealed with the catheter 51 to provide communication between its chamber 52 and the opening 54 of the catheter 51.

The end 36 of the transport unit 40 may now be moved to its contracted position shown in FIG. 2 and securely locked. The inward movement of the piston or plunger 60 results in the advancement of the sensing head 12 so that it extends out of the end 56 of the catheter 51 and into the blood system in which measurements of partial pressure of oxygen are to be obtained and monitored. An electrical measuring apparatus (not shown) is electrically joined to the connector 34 of the terminal 36 and provides a bias voltage potential to the conductors and electrodes 22, 26 of the sensing head 12 of 0.6 volt.

Since the membrane 94 is pervious to oxygen in the blood system, the oxygen passes therethrough to the electrolyte 91 resulting in polarographic action. As well known, the presence of oxygen at the polarographic sensing head 12 produces a current which may be calibrated to show the partial pressure of oxygen. Such current flow is delivered to an indicating means (not shown) providing output readings which may be calibrated by reference to measurements taken of blood samples by means of a conventional gas analyzer.

The catheter system for blood gas monitoring has been most effective and useful during and after major cardiovascular and pulmonary operations by providing continuous indications of oxygen tension in the blood correlated to within 12 % of the values obtained by conventional gas analyzers. Such indications have followed faithfully stepwise changes in oxygen tension of inspired gas. It has been found that the catheter system could be left in-situ in patients for periods of 24 hours and more, proving the system to be of value for monitoring arterial partial oxygen pressure during and after major cardiovascular and pulmonary surgery and providing helpful information for the controlling of artificial ventilation.

The system provides a great advantage over prior art, by having a polarographic sensing head with an extended shelf life. This is achieved by providing the head with its electrolyte in a dry condition when not in use, while the head may be readily activated for use by placing same in a saline solution. The sensing head 12 can also be activated by placing same in the blood system, although the preactivation by immersion in the saline solution is preferred.

The in-situ calibration is also advantageous in that it permits making allowance for flow, temperature, and positioning artifacts. Calibration is readily accomplished by withdrawing blood samples through the catheter 51 by a syringe attached to the port 68 of the transport unit 40. In addition to removing such blood samples, other desirable fluids may be infused through the port 68, so that the catheter system does not interfere with other functions which are to be accomplished by use of the catheter, which may have previously been implanted for such purposes, and is utilized by the catheter system.

It will be obvious to those skilled in the art that the invention disclosed may find wide application with appropriate modification to meet individual design circumstances, but without substantial departure from the essence of the invention.

What is claimed is:
1. The method of making a polarographic sensing means for sensing gas tension in a fluid system comprising the steps of:
   a. forming a body with first and second spaced electrodes providing exposed surfaces at a region of said body,
   b. affixing a deactivated anhydrous electrolytic material over the exposed surfaces of said electrodes on said body, and
   c. securing with said body a membrane which is semipervious to water enclosing the electrolytic material and the exposed surfaces of said electrodes,
whereby the sensing means produced is in a deactivated state and can be activated prior to use by the application of an aqueous solution to the outside of its membrane.

2. The method of claim 1 including the step of
   d. applying an aqueous solution to the outside of the membrane for activating said electrolytic material of the sensing means by passage of water through said membrane prior to utilization of the sensing means.

3. The method of claim 1 in which the anhydrous electrolytic material is affixed over the epoxy surfaces of said electrodes by applying wet electrolytic material on the body over the said electrodes and allowing same to dry prior to enclosing the electrolytic material by said membrane.

4. The method of claim 3 in which the wet electrolytic material is potassium chloride gel which is dried to crystaline form.

5. The method of claim 1 in which the membrane is formed by applying a solution of polyvinyl formal to the body over said anhydrous electrolytic material and drying same to form a coating which is semi-pervious to water and pervious to oxygen in an aqueous solution.

6. The method of claim 5 in which the membrane is formed by the additional step of applying a silicone solution over the polyvinyl formal coating and drying same to form an outer coating of said membrane.

7. The method of claim 1 in which the body with first and second spaced electrodes is formed by
   a. providing a cylindrical mold having an opening along its longitudinal axis and positioning in spaced axial extending relationship therein said first and second conductors,
   b. filling the opening of said mold about said conductors with an epoxy material in unset form and permitting said epoxy material to set and harden,
   c. severing the mold, epoxy material, and conductors extending therethrough, along a plane substantially perpendicular to the longitudinal axis of said mold providing said conductors with exposed surfaced at a flat surface region of said body, and
   d. removing the remaining mold from about said body.

8. The method of claim 7 in which a wet electrolytic material comprising potassium chloride gel is applied to the flat surface region of said epoxy body over the exposed surfaces of said conductors and dried to crystaline form, the membrane is formed by applying a solution of polyvinyl formal to the body over said dried electrolytic material and drying same to form a coating which is semipervious to water and pervious to oxygen in an aqueous solution, and applying a silicone solution over the polyvinyl formal coating and drying same to form an outer coating of said membrane.

9. The method of claim 8 including the step of applying an aqueous solution to the outside of said membrane for activating said electrolytic material of the sensing means by the passage of water through said membrane prior to utilization of the sensing means.

* * * * *